United States Patent [19]

Goeddel et al.

[11] Patent Number: 5,460,811
[45] Date of Patent: Oct. 24, 1995

[54] MATURE HUMAN FIBROBLAST INTERFERON

[75] Inventors: David V. Goeddel; Roberto Crea, Burlingame, Calif.

[73] Assignee: Genentech, Inc., South San Francisco, Calif.

[21] Appl. No.: 365,284

[22] Filed: Jun. 12, 1989

Related U.S. Application Data

[60] Continuation of Ser. No. 889,722, Jul. 28, 1986, abandoned, which is a division of Ser. No. 291,892, Aug. 11, 1981, abandoned, which is a continuation-in-part of Ser. No. 190,799, Sep. 25, 1980, abandoned.

[51] Int. Cl.$^6$ ............................ C07K 15/26; A61K 37/66
[52] U.S. Cl. ..................... 424/85.6; 424/85.4; 530/351
[58] Field of Search .................... 530/351; 424/85.6, 42485.4

[56] References Cited

U.S. PATENT DOCUMENTS

| | | | |
|---|---|---|---|
| 4,262,090 | 4/1981 | Colby et al. | 435/97 |
| 4,289,689 | 9/1981 | Friesen et al. | 260/112 R |
| 4,332,892 | 6/1982 | Ptashne et al. | 435/172 |
| 4,342,832 | 8/1982 | Goeddel et al. | 435/172 |
| 4,418,149 | 4/1983 | Ptashne et al. | 435/172 |
| 4,874,702 | 10/1989 | Fiers et al. | 435/172 |
| 5,015,730 | 5/1991 | Friesen et al. | 530/351 |

FOREIGN PATENT DOCUMENTS

| | | |
|---|---|---|
| 6694 | 1/1980 | European Pat. Off. . |
| 2007676 | 5/1979 | United Kingdom . |

OTHER PUBLICATIONS

Darnell et al. (Darnell), Molecular Cell Biology, "Golgi Vesicles: Sorting and Glycosylation of Secretory and Membrane Proteins", Second Edition, pp. 661–667 (1990).
Houghton et al., Nature 285:536 (published Jun. 19, 1980).
Goeddel et al., Nature 287:411–416 (published Oct. 2, 1980).
Horoszewicz et al., Cancer Treatment Rep. 62:1899–1906 (1978)
Stewart II et al., Virology 97:473–476 (1979).
Pestka et al., Proc. Nat'l Acad. Sci USA 72: 3898–3901 (1975).
Reynolds et al., Proc. Nat'l Acad. Sci. USA 72: 4881–4885 (1975).
Cavalieri et al., Proc. Nat'l Acad. Sci. USA 74: 4415–4419 (1977).
Stewart II, in The Interferon System (Springer–Verlag, New York, 1979), pp. 90–96, 335, 386 and 389.
Grob et al., Biochemistry 18: 5782–86 (1979).
Havell et al., Virology 63: 475–83 (1975).
Houghton et al., Nucleic Acids Res. 8: 1913–31 (1980).
Bose et al., J. Biol. Chem. 251: 1659–62 (1976).
Davey et al., Biochemistry 15: 704–13 (1976).
Eagon et al., J. Biol. Chem. 252: 2372–83 (1977).
Mizrahi et al., J. Biol. Chem. 253: 7612–15 (1978).
Stewart et al., Proc. Natl. Acad. Sci. USA 74: 4200–04 (1977).
Struck et al., In *The Biochemistry of Glycoproteins and Proteoglycans*, Plenum Press (W. J. Lennarz ed.), 1980, pp. 35–83.
Taniguchi et al., Proc. Japan Acad. 55(Ser.B):464–469 (1979).
Taniguchi et al., Gene 10:11–15 (published May 19, 1980).
Taniguchi et al., Proc. Nat'l. Acad. Sci. USA 77:4003–4006 (published Aug. 13, 1980).
Taniguchi et al., Proc. Nat'l. Acad. Sci. USA 77:5230–5233 (published Oct. 15, 1980).
Taniguchi et al., Nature 285:547–549 (published Jun. 19, 1980).
Derynck et al., Nature 285:542–547 (published Jun. 19, 1980).
Derynck et al., Nature 287:193–197 (published Sep. 18, 1980).
Guarente et al., Science 209:1428–1430 (published Sep. 19, 1980).
Anonymous, Research Disclosure (Jul. 1979).
Houghton et al., Nucleic Acids Res. 8(13):2885–2894 (published Jul. 14, 1980).
Goeddel et al., Nucleic Acids Res. 8(18):4057–4074 (published Sep. 25, 1980).
Goeddel et al., Nature 281:544–548 (1979)
Chang et al., Nature 275:617–624 (1978).

Backman et al., Cell 13:65–71 (1978).
Knight, Proc. Nat'l Acad. Sci. USA 73(21):520–523 (1976).
Tan et al., J. Biol. Chem. 244:8067–8073 (1979).
Berthold et al., J. Biol. Chem. 253(14):5206–5212 (1978).
Knight et al., Science 207:525–527 (1980).
Reynolds et al., Biochem. Biophys. Res. Comm. 63(1)107–112 (1977).
Havell et al., J. Biol. Chem. 252(12):4425–4427 (1977).
Cavalieri et al., Proc. Nat'l. Acad. Sci. USA 74:3287–3291 (1977).
Pestka et al., Ann. Rev. New York Acad. Sci. 284:697–702 (1977).
Content et al., Virology 122:466–470 (1982).
Roberts et al., Proc. Nat'l. Acad. Sci. USA 76:760–764 (1979).
Roberts et al., Proc. Nat'l. Acad. Sci. USA 76:5596–5600 (1979).
Guarente et al., Cell, 20:543–553 (1980).
Backman et al. Cell 13 pp. 65–71 (1978).
Taniguchi et al. Gene 10 pp. 11–15 (1980).
Taniguchi et al. Proc. Japan Acad. 55 (Ser.B) (1979) pp. 464–469.

Goeddel et al. Nature 281 pp. 544–548 (1979).
Chang et al. Nature 275 pp. 617–624 (1978).
Derynck et al. Nature 285 pp. 542–547 (1980).

*Primary Examiner*—Garnette D. Draper
*Assistant Examiner*—Shelly Guest Cermak

[57] ABSTRACT

A cDNA library is constructed using mRNA from human fibroblasts induced with poly(I):poly(C). A bacterial clone containing fibroblast interferon cDNA sequences identified by hybridization to a cDNA probe synthesized using deoxyoligonucleotide primers which hybridize to fibroblast interferon mRNA specifically. Expression plasmids are constructed which permit the synthesis in *E. coli* of $8 \times 10^7$ units of human fibroblast interferon per liter of culture. The bacterially produced fibroblast interferon is indistinguishable from authentic human fibroblast interferon by several critieria.

6 Claims, 6 Drawing Sheets

```
                          1   2   3   4
Protein                   Met-Ser-Tyr-Asn-
                                G
                                A
                (5') AUG-UC U -UA U -AA U    (16 combinations)
                                C       C      C
                (5') AUG-AG U -UA U -AA C    ( 8 combinations)
                            C     C      U
                     ATT- A TA- T GA-CAT     Pool 1
                         G     C
                     ATT- A TA- A GA-CAT     Pool 2
                         G     G
Complementary DNA    ATT- A TA- A CT-CAT     Pool 3
primers                  G     G
                     GTT- A TA- T GA-CAT     Pool 4
                         G     C
                     GTT- A TA- A GA-CAT     Pool 5
                         G     G
                     GTT- A TA- A CT-CAT     Pool 6
                         G     G
```
FIG. 1
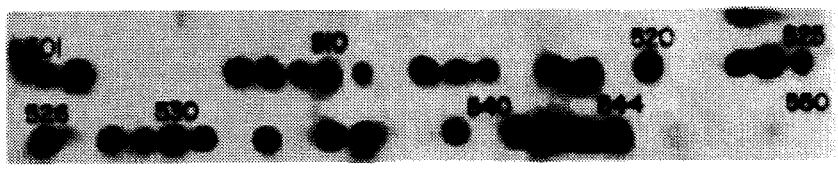
FIG. 2A
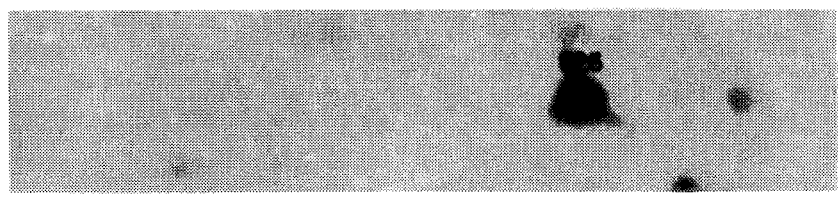
FIG. 2B
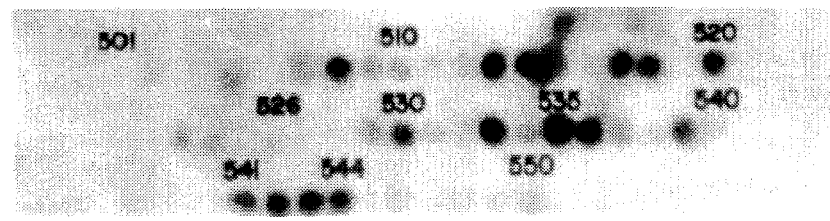
FIG. 2C

FIG. 3

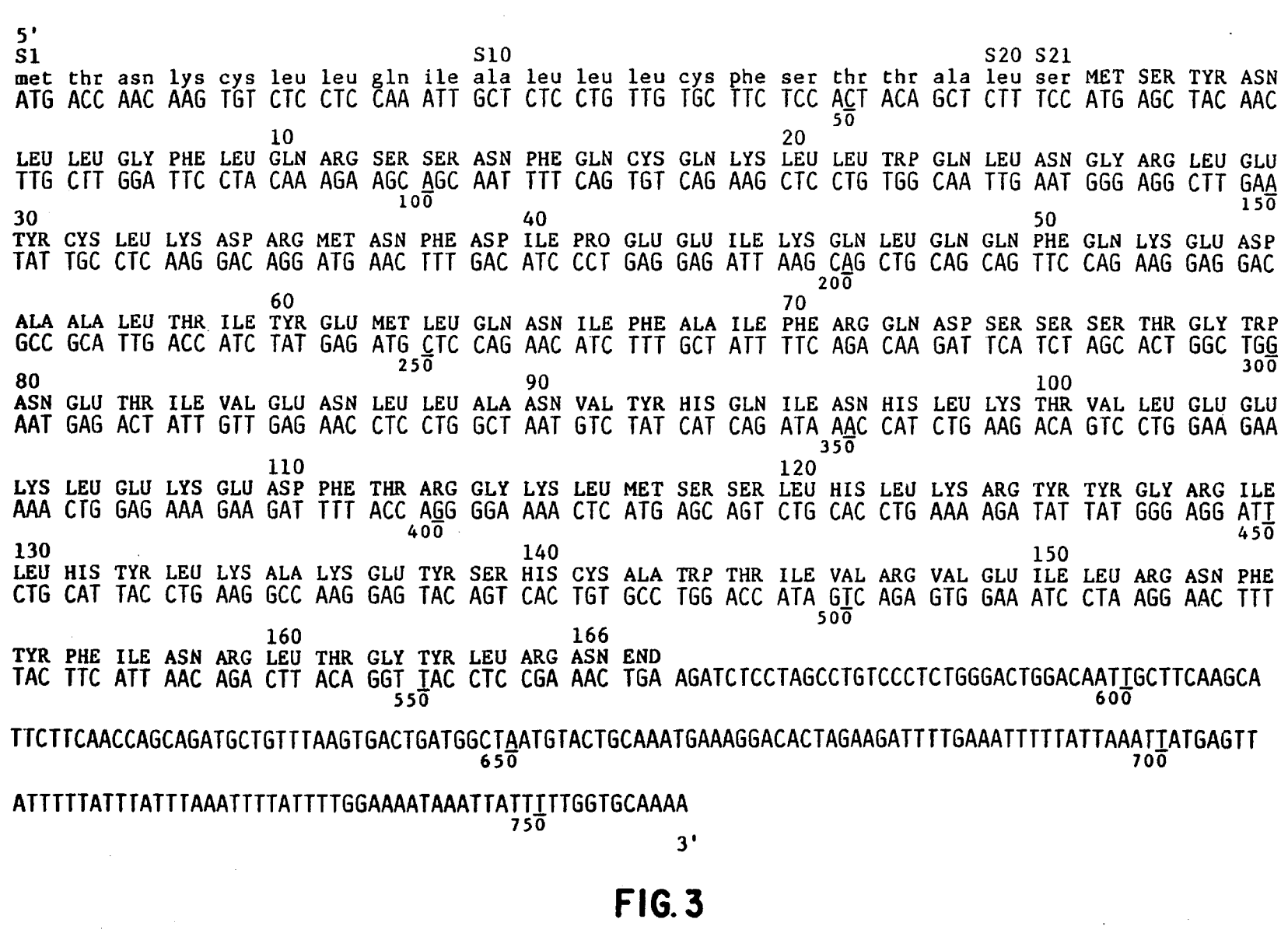

```
5'
S1                                              S10
met thr asn lys cys leu leu gln ile ala leu leu cys phe ser thr ala leu ser met ser tyr asn
ATG ACC AAC AAG TGT CTC CTC CAA ATT GCT CTG TTG TGC TTC TCC ACT GCT CTT TCC ATG AGC TAC AAC
                          10                         20                         S20 S21

LEU GLY PHE LEU ARG GLN SER ASN PHE GLN LYS LEU LEU TRP GLN LEU ASN GLY ARG LEU GLU
TTG GGA TTC CTA CAA CAA AGC AAT TTT CAG AAG CTC CTG TGG CAA TTG AAT GGG AGG CTT GAA
        30                      40                      50                   150

TYR CYS LEU LYS ASP ARG MET ASN PHE ASP SER ARG GLN ASP SER SER THR GLY TRP
TAT TGC CTC AAG GAC AGG ATG AAC TTT GAC TCA AGA CAA GAT TCA TCT AGC ACT GGC TGG
              60                     70                                        300

ALA ALA LEU THR ILE TYR GLU MET LEU PHE ALA ILE ASN HIS LEU HIS LYS ARG VAL LEU GLU GLU
GCA GCA TTG ACC ATC TAT GAG ATG CTC TTT GCT ATT CAG AAC CAT CTG AAG AGA GTC CTG GAA GAA
                          250                     200                              450

ASN GLU THR ILE VAL GLU ASN LEU LEU ALA ASN VAL TYR HIS TYR ILE ASN LYS ARG TYR TYR GLY ARG ILE
AAT GAG ACT ATT GTT GAG AAC CTC CTG GCT AAT GTC TAT CAT CAG ATA AAC CTG AAG AGA TAT TAT GGG AGG ATT
        80                      90                   350                       150

LYS LEU GLU LYS GLU LYS ALA ASP PHE THR ARG GLY LYS TYR SER HIS CYS ALA TRP THR ILE VAL GLU LEU ARG ASN PHE
AAA CTG GAG AAA GAA AAG GCC GAT TTT ACC AGG GGA TAC AGT CAC TGT GCC TGG ACC ATA GTC GAA CTA AGG AAC TTT
              110                     120                     140                     500

130
LEU HIS TYR LEU LYS GLU GLU LYS TYR SER LEU ARG 166
CTG CAT TAC CTG AAG GAG GAA AAG TAC AGT CTC CGA GGT TAC CTT ACA AGA AAT TGA
              550                              166 ASN END
                                                    AAC AAC

TYR PHE ILE ASN ARG LEU THR GLY TYR LEU ARG ASN
TAC TTC ATT AAC AGA CTT ACA GGT TAC CTC CGA AAC TGA AGATCTCCTAGCCTGTCCCTCTGGGACTGACAATGCTTCAAGCA
        160                                                                                    600

TTCTTCAACCAGCAGATGCTGTTTAAGTGACTGATGGCTAATGTACTGCAAATGAAGGACACTAGAAGATTTTGAAATTTTATTAAATTATGAGTT
                                     650                                                      700

ATTTTATTTATTAAATTTTATTTTGGAAAATAAATTTATTTTTGGTGCAAAA
                  750

3'
```

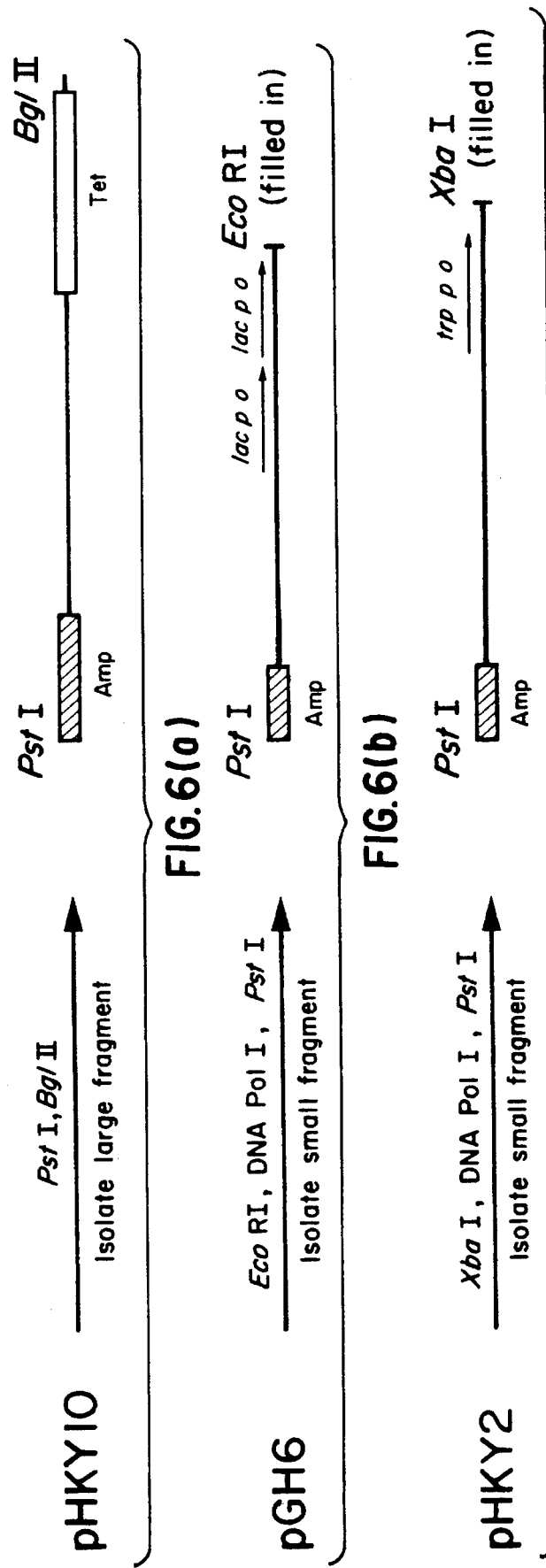

MATURE HUMAN FIBROBLAST INTERFERON

CROSS-REFERENCE TO RELATED APPLICATION

This is a continuation of application Ser. No. 889,722, filed Jul. 28, 1986, now abandoned which is a divisional of application Ser. No. 291,892, now abandoned filed Aug. 11, 1981, which is a continuation-in-part of application Ser. No. 190,799, filed Sep. 25, 1980, now abandoned.

FIELD OF THE INVENTION

This invention relates to the microbial production, via recombinant DNA technology, of human fibroblast interferon for use in the treatment of viral and neoplastic diseases, and to the means and end products of such production.

BACKGROUND OF THE INVENTION

The publications and other materials referred to herein to illuminate the background of the invention and, in particular cases, to provide additional detail respecting its practice are incorporated herein by reference and, for convenience, are numerically referenced in the following text and respectively grouped in the appended bibliography.
Recombinant DNA Technology With the advent of recombinant DNA technology, the controlled microbial production of an enormous variety of useful polypeptides has become possible. Already in hand are bacteria modified by this technology to permit the production of such polypeptide products such as somatostatin, the (component) A and B chains of human insulin, human growth hormone. More recently, recombinant DNA techniques have been used to occasion the bacterial production of proinsulin, thymosin alpha 1, (an immune potentiating substance produced by the thymus) and leukocyte interferon.

The workhorse of recombinant DNA technology is the plasmid, a non-chromosomal loop of double-stranded DNA found in bacteria and other microbes, oftentimes in multiple copies per cell. Included in the information encoded in the plasmid DNA is that required to reproduce the plasmid in daughter cells (i.e., a "replicon") and ordinarily, one or more selection characteristics such as, in the case of bacteria, resistance to antibiotics which permit clones of the host cell containing the plasmid of interest to be recognized and preferentially grown in selective media. The utility of plasmids lies in the fact that they can be specifically cleaved by one or another restriction endonuclease or "restriction enzyme", each of which recognizes a different site on the plasmidic DNA. Thereafter heterologous genes or gene fragments may be inserted into the plasmid by endwise joining at the cleavage site or at reconstructed ends adjacent to the cleavage site. DNA recombination is performed outside the cell, but the resulting "recombinant" plasmid can be introduced into it by a process known as transformation and large quantities of the heterologous gene-containing recombinant plasmid obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression.

Expression is initiated in a region known as the promoter which is recognized by and bound by RNA polymerase. In some cases, as in the tryptophan or "trp" promoter preferred in the practice of the present invention, promoter regions are overlapped by "operator" regions to form a combined promoter-operator. Operators are DNA sequences which are recognized by so-called repressor proteins which serve to regulate the frequency of transcription initiation at a particular promoter. The polymerase travels along the DNA, transcribing the information contained in the coding strand from its 5' to 3' end into messenger RNA which is in turn translated into a polypeptide having the amino acid sequence for which the DNA codes. Each amino acid is encoded by a nucleotide triplet or "codon" within what may for present purposes be referred to as the "structural gene", i.e. that part which encodes the amino acid sequence of the expressed product. After binding to the promoter, the RNA polymerase first transcribes nucleotides encoding a ribosome binding site, then a translation initiation or "start" signal (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, in bacteria ordinarily as the mRNA is being formed, and themselves produce the encoded polypeptide, beginning at the translation start signal and ending at the previously mentioned stop signal. The desired product is produced if the sequences encoding the ribosome binding site are positioned properly with respect to the AUG initiator codon and if all remaining codons follow the initiator codon in phase. The resulting product may be obtained by lysing the host cell and recovering the product by appropriate purification from other bacterial protein.
Fibroblast Interferon Human fibroblast interferon (FIF) is an antiviral protein which also exhibits a wide range of other biological activities (see ref. 1 for review). It has reportedly been purified to homogeneity as a single polypeptide of 19,000–20,000 molecular weight having a specific activity of 2 to $10 \times 10^8$ units/mg (2,3). The sequence of the 13 $NH_2$-terminal amino acids of FIF has been determined (4). Houghton et al. (5) have used synthetic deoxyoligonucleotides (predicted from this amino acid sequence) to determine the sequence of the 276 5'-terminal nucleotides of FIF mRNA. Taniguchi et al. (6) and Derynck et al. (7) have recently employed RNA selection procedures to identify cloned cDNA copies of FIF mRNA in *E. coli*. See also Taniguchi et al., *Gene* 10, 11 (1980) and *Proc. Natl. Acad. Sci.* (*U.S.A.*) 77, 5230 (1980) and *Nature* 285, 547 (1980).

While isolation from donor fibroblasts has provided sufficient material for partial characterization and limited clinical studies with homogeneous fibroblast interferon, it is a totally inadequate source for the amounts of interferon heeded for large scale clinical trials and for broad scale prophylactic and/or therapeutic use thereafter. Indeed, presently clinical investigations employing human fibroblast-derived interferon in antitumor and antiviral testing have principally been confined to crude (<1 percent pure) preparations of the material, and long lead times for the manufacture of sufficient quantities, even at unrealistic price levels, have critically delayed investigation on an expanded front.

We perceived that application of recombinant DNA technology would be the most effective way of providing large quantities of fibroblast interferon which, despite the absence in material so produced of the glycosylation characteristic of human-derived material, could be employed clinically in the treatment of a wide range of viral and neoplastic diseases.

More particularly, we proposed and have since succeeded in producing mature human fibroblast interferon microbially, by constructing a gene therefor which could then be inserted in microbial expression vehicles and expressed under the control of microbial gene regulatory controls.

Our approach to obtaining a fibroblast gene involved the following tasks:

1. Partial amino acid sequences would be obtained by characterization of fibroblast interferon purified to essential homogeneity, and sets of synthetic DNA probes constructed whose codons would, in the aggregate, represent all the possible combinations capable of encoding the partial amino acid sequences.

2. Bacterial colony banks would be prepared containing cDNA from induced messenger RNA. The probes of part (1) would be used to prime the synthesis of radio-labelled single stranded cDNA for use as hybridization probes. The synthetic probes would hybridize with induced mRNA as template and be extended by reverse transcription to form induced, radio-labelled cDNA. Clones from the colony bank that hybridized to radio-labelled cDNA obtained in this manner would be investigated further to confirm the presence of a full-length interferon encoding gene. Any partial length putative gene fragment obtained would itself be used as a probe for the full-length gene.

3. The full-length gene obtained above would be tailored, using synthetic DNA, to eliminate any leader sequence that might prevent microbial expression of the mature polypeptide and to permit appropriate positioning in an expression vehicle relative to start signals and the ribosome binding site of a microbial promoter. Expressed interferon would be purified to a point permitting confirmation of its character and determination of its activity notwithstanding the absence of glycosylation.

SUMMARY OF INVENTION

A series of replicable plasmidic expression vehicles have been constructed which direct the high level synthesis in transformant microorganisms of a mature polypeptide with the properties of authentic human fibroblast interferon. The product polypeptide exhibits the amino acid sequence of such interferon and is active in in vitro testing despite the lack of glycosylation characteristic of the human-derived material. Reference herein to the expression of "mature fibroblast interferon," connotes the bacterial or other microbial production of an interferon molecule unaccompanied by associated glycosylation and the presequence that immediately attends mRNA translation of the human fibroblast interferon genome. Mature fibroblast interferon, according to the present invention, is immediately expressed from a translation start signal (ATG) which also encodes the first amino acid codon of the natural product. The presence or absence of the methionine first amino acid in the microbially expressed product is governed by a kinetic phenomenon dependent on fermentation growth conditions and/or levels of expression in the transformant host. Mature fibroblast interferon could be expressed together with a conjugated protein other than the conventional leader, the conjugate being specifically cleavable in an intra- or extracellular environment. See British Patent Publication No. 2007676A. Finally, the mature interferon could be produced in conjunction with a microbial "signal" peptide which transports the conjugate to the cell wall, where the signal is processed away and the mature polypeptide secreted.

DESCRIPTION OF THE FIGURES

FIG. 1 depicts the protein sequence information used to design degenerate dodecanucleotide primers. Below the protein sequence are corresponding mRNA sequences and six pools of complementary deoxyoligonucleotide primers.

FIGS. 2A–C are autoradiographs of nitrocellulose-bound plasmid DNA prepared from some of the 600 bacterial transformants having DNA from the fibroblast cDNA library. The plasmid DNA of the nitrocellulose membrane was hybridized with either probe A, B, or C.

FIG. 3 presents DNA sequence of the cDNA insert of clone pFIF3 as determined by the Maxam-Gilbert procedure. The deduced protein sequence in printed above the DNA sequence.

FIG. 6, and 6a, 6b, 6c schematically depicts the construction of plasmids coding for the direct expression of mature fibroblast interferon. Restriction sites and residues are as shown ("Pst I", etc.). "Ap$^R$" and "Tc$^R$" connote portions of the plasmid (s) which express, respectively, ampicillin and tetracycline resistance. The legend "p o" is an abbreviation for "promoter operator."

DESCRIPTION OF THE PREFERRED EMBODIMENTS

A. Microorganisms Employed

Figure 4:
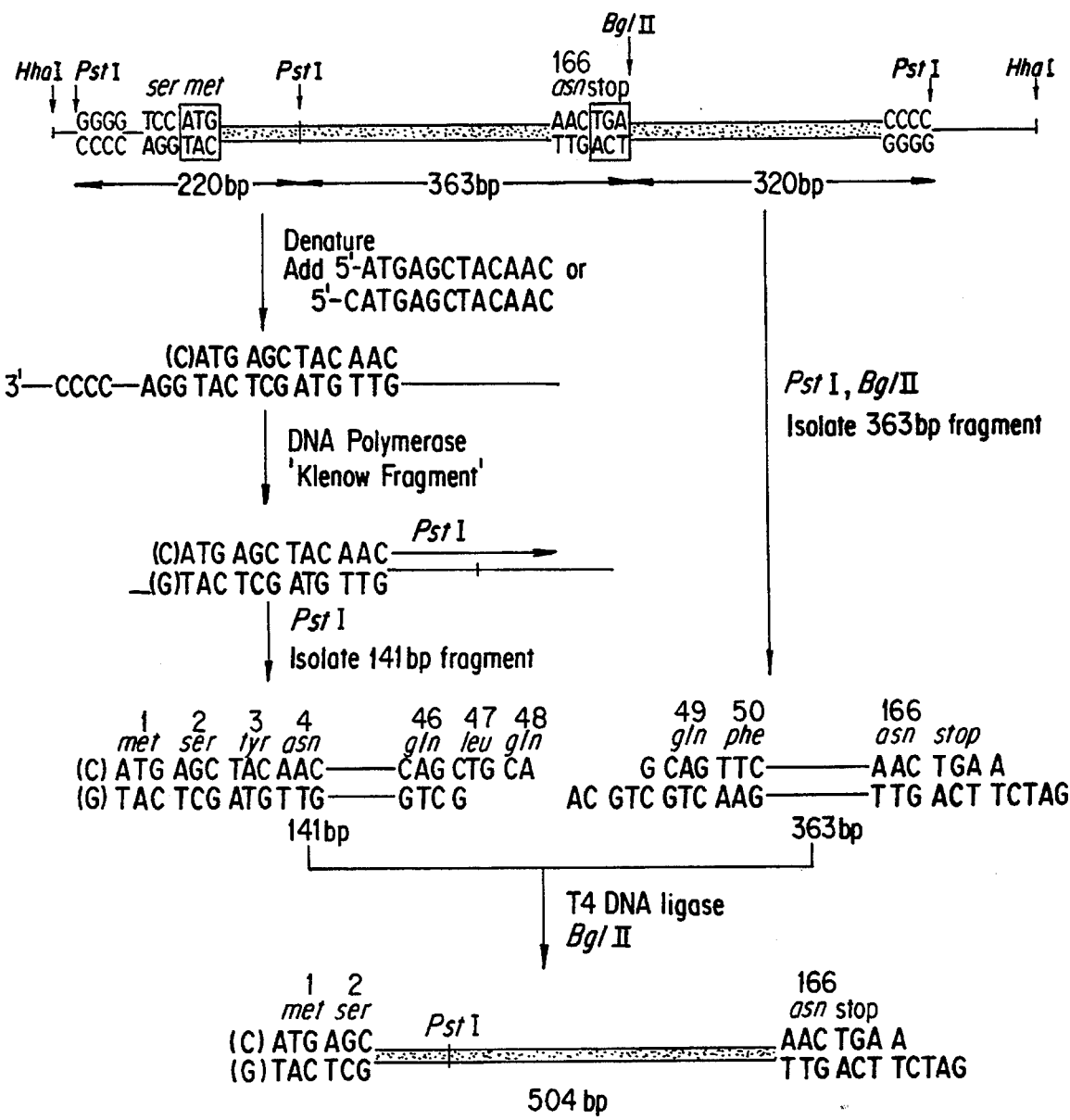
FIG. 4 is a diagram showing the approach used to remove the signal peptide coding regions from pFIF3.

The work described involved used of the microorganism: E. coli K-12 strain 294 (end A, thi$^-$, hsr$^-$, hsm$_k{}^+$), as described in British Patent Publication No. 2055382 A. This strain has been deposited on Oct. 28, 1978 with the American Type culture Collection, which is located at 12301 Parklawn Drive. Rockville, Md. 20852, and given ATCC Acession No. 31446. All recombinant DNA work was performed in compliance with applicable guidelines of the National Institutes of Health.

The invention, in its most preferred embodiments, is described with reference to E. coli, including not only strain E. coli K-12 strain 294, defined above, but also other known E. coli strains such as E. coli B, E. coli x 1776 and E. coli W 3110, or other microbial strains many of which are deposited and (potentially) available from recognized microorganism depository institutions, such as the American Type Culture Collection (ATCC)—cf. the ATCC catalogue listing. See also German Offenlegungschrift 2644432. These other microorganisms include, for example, Bacilli such as Bacillus subtilis and other enterobacteriaceae among which can be mentioned as examples Salmonella typhimurium and Serratia marcesans, utilizing plasmids that can replicate and express heterologous gene sequences therein. Yeast, such as Saccharomyces cerevisiae, may also be employed to advantage as host organism in the preparation of the interferon proteins hereof by expression of genes coding therefor under the control of a yeast promoter.
MATERIALS AND METHODS
General methods.

Restriction enzymes were purchased from New England Biolabs and used as directed. Plasmid DNA was prepared by a standard cleared lysate procedure (8) and purified by column chromatography on Biogel A-50M (Bio-Rad). DNA sequencing was performed using the method of Maxam and Gilbert (9). DNA restriction fragments were isolated from polyacrylamide gels by electroelution. DNA fragments were radiolabeled for use as hybridization probes by the random calf thymus DNA priming procedure of Taylor et al. (10). In situ colony hybridizations were performed by the Grunstein-Hogness procedure (11).

Chemical synthesis of deoxyoligonucleotides.

The deoxyoligonucleotides were synthesized by the modified phosphotriester method in solution (12), using trideoxynucleotides as building block (13). The material and general procedures were similar to those described (14). The six pools of primers (Fib 1–6) containing four dodecanucleotides each were obtained by separately coupling two hexamer pools (of two different 5'-terminal sequences each) with three different hexamer pools (of two different 3'-terminal sequences each).

Induction of fibroblasts.

Human fibroblasts (cell line GM-2504A) were grown as described previously (15). Growth medium (Eagles's minimal essential medium containing 10 percent fetal calf serum) was removed from roller bottles (Corning, 850 cm$^2$) and replaced with 50 ml growth medium containing 50 µg/ml of poly (I):poly (C) (PL Biochemicals) and 10 µg/ml cycloheximide. This induction medium was removed after 4 hours at 37° C. and cell monolayers were washed with PBS (0.14M NaCl, 3 mM KCl, 1.5 mM $KH_2PO_4$, 8 mM $Na_2HPO_4$). Each bottle was incubated at 37° C. with 10 ml of a trypsin-EDTA solution (Gibco 610-5305) until cells were detached, and fetal calf serum was added to a concentration of 10 percent. Cells were spun for 15 minutes at 500× g and pellets were resuspended in PBS, pooled, and resedimented. Cells were frozen in liquid nitrogen. Approximately 0.17 g of cells were obtained per roller bottle.

Preparation and assay of interferon mRNA.

Poly extraction and oligo(dT)-cellulose chromatography as described elsewhere (16). The poly (A) containing RNA was enriched for interferon mRNA by centrifugation on a linear 5 percent to 20 percent (w/v) sucrose gradient. The RNA samples were heated to 80° C. for 2 minutes, rapidly cooled, layered over the gradient, and centrifuged for 20 hours at 30,000 rpm at 4° C. in a Beckman SW-40 rotor. Fractions were collected, ethanol precipitated, and dissolved in $H_2O$.

One microgram samples of mRNA were injected into *Xenopus laevis* oocytes as described previously (17,18). The injected oocytes were incubated 24 hours at 21° C., homogenized, and centrifuged for 5 minutes at 10,000× g. The interferon in the supernatant was determined by the cytopathic effect (CPE) inhibition assay (1) using Sindbis virus and human diploid (WISH) cells. Interferon titers of 1,000 to 6,000 units recovered (NIH reference standard) per microgram of RNA injected were routinely obtained for the 12S species of mRNA.

Synthesis and cloning of cDNA.

Single stranded cDNA was prepared in 100 µl reactions containing 5 µg of 12S fraction mRNA, 20 mM Tris-HCl (pH 8.3), 20 mM KCl, 8 mM $MgCl_2$, 30 mM β-mercaptoethanol, 100 µCi of ($\alpha^{32}$p)dCTP (Amersham) and 1 mM dATP, dCTP, dGTP, dTTP. The primer was the synthetic Hind III decamer dCCAAGCTTGG (19), which had been extended at the 3' terminus with about 20 to 30 deoxythymidine residues using terminal deoxynucleotidyl transferase (20). 100 units of AMV reverse transcriptase were added and the reaction mixture was incubated at 42° C. for 30 minutes. The second strand DNA synthesis was carried out as described previously (21). The double stranded cDNA was treated with 1200 units of S1 nuclease (Miles Laboratories) for 2 hours at 37° C. in 25 mM sodium acetate (pH 4.5), 1 mM $ZnCl_2$, 0.3M NaCl. After phenol extraction the mixture was separated electrophoretically on an 8 percent polyacrylamide gel. cDNA (~0.5 µg) ranging from 500 to 1500 base pairs in size was recovered by electroelution. A 20 ng aliquot was extended with deoxyC residues using terminal deoxynucleotidyl transferase (20), and annealed with 100 ng of pBR322 which had been cleaved with Pst I and tailed with deoxyG residues (20). The annealed mixture was used to transform *E. coli* k-12 strain 294 (22) by a published procedure (23). Strain 294 was used throughout in the work described here, and has been deposited with the American Type Culture collection, accession no. 31446.

Preparation of induced and uninduced $^{32}$p-cDNA probes.

5 µg of 12S mRNA were combined with either 2 µg of oligo $(dT)_{12-18}$ (Collaborative Research) or 5 µg of each synthetic primer pool (Fib 1 to Fib 6) in 60 µl of 10 mM Tris-HCl (ph 8), 1 mM EDTA. The mixtures were boiled 3 minutes, and quenched on ice. 60 µl of 40 mM Tris-HCl (pH 8.3), 40 mM KCl, 16 mM $MgCl_2$,60 mM β-mercaptoethanol, 1 mM dATP, dGTP, dTTP and $5 \times 10^{-7}$M ($\alpha$-$^{32}$p) dCTP (Amersham, 2,000–3,000 Ci/mmole) was added to each template-primer mix at 0° C. After the addition of 100 units of AMV reverse transcriptase, the reactions were incubated at 42° C. for 30 minutes and purified by passage over 10 ml Sephadex G-50 columns. The products were treated with 0.3N NaOH for 30 minutes at 70° C., neutralized, and ethanol precipitated.

The $^{32}$p-cDNAs were combined with 100 µg of poly (A) mRNA from uninduced fibroblasts in 50 µl of 0.4M sodium phosphate (pH6.8), 0.1 percent SDS. The mixtures were heated at 98° C. for 5 minutes and allowed to anneal 15 hours at 45° C. The DNA-RNA hybrids. (containing uninduced cDNA sequences) were separated from single-stranded DNA (induced cDNA sequences) by chromatography on hydroxyapatite as described by Galau et al. (24). The DNA-RNA hybrids were treated with alkali to remove RNA.

Screening of recombinant plasmids with $^{32}$p-cDNA probes.

Approximately 1 µg samples of plasmid DNA were prepared from individual transformants by a published procedure (25). The DNA samples were linearized by digestion with Eco RI, denatured in alkali, and applied to each of three nitrocellulose filters (Schleicher and Schuell, BA85) by the dot hybridization procedure (26). The filters were hybridized with the $^{32}$p-cDNA probes for 16 hours at 42° C. in 50 percent formamide, 10× Denhardt's solution (27), 6×SSC, 40 mM Tris-HCl (pH 7.5), 2 mM EDTA, 40 µg/ml yeast RNA. Filters were washed with 0.1×SSC, 0.1 percent SDS twice for 30' at 42° C., dried, and exposed to Kodak XR-2 x-ray film using Dupont Lightning-Plus intensifying screens at −80° C.

Construction of plasmids for direct expression of FIF.

The synthetic primers I (dATGAGCTACAAC) and II (dCATGAGCTACAAC) were phosphorylated using T4 polynucleotide kinase and (γ-$^{32}$.P)ATP (Amersham) to a specific activity of 700 Ci/mmole as described previously (28). Primer repair reactions were performed as follows: 250 pmoles of the $^{32}$P-primers were combined with 8 µg (10 pmole) of a 1200 bp Hha I restriction fragment containing the FIF cDNA sequence. The mixture was ethanol precipitated, resuspended in 50 µl $H_2O$, boiled 3 minutes, quenched in a dry ice-ethanol bath, and combined with a 50 µl solution of 20 mM Tris-HCl (pH 7.5), 14 mM $MgCl_2$, 120 mM NaCl, 0.5 mM dATP, dCTP, dGTP, dTTP at 0° C. 10 units of DNA polymerase I Klenow fragment (Boehringer-Mannheim) were added and the mixture was incubated at 37° C. for 4½ hours. Following extraction with phenol/$CHCl_3$ and restriction with Pst I, the desired product was purified on a 6 percent polyacrylamide gel. Subsequent ligations were done at room temperature (cohesive termini) or 4° C. (blunt ends) using previously detailed conditions (21,28).

Assay for interferon expression in E. coli.

Bacterial extracts were prepared for IF assay as follows: One ml cultures were grown overnight in LB (29) containing 5 μg/ml tetracycline, then diluted into 25 ml of M9 medium (29) containing 0.2 percent glucose, 0.5 percent casamino acids and 5 μg/ml tetracycline. 10 ml samples were harvested by centrifugation when $A_{550}$ (Absorbance at 500 nanometers) reached 1.0. The cell pellets were quickly frozen in a dry ice-ethanol bath and cleared lysates were prepared as described by Clewell (8). Interferon activity in the supernatants was determined by comparison with NIH FIF standards using cytopathic effect (CPE) inhibition assays as reviewed previously (1). Two different assays were used: (a) WISH (human amnion) cells were seeded in microtiter dishes. Samples were added 16 to 20 hours later and diluted by serial 2-fold dilution. Sindbis virus was added after at least 3 hours in incubation. Plates were stained 20 to 24 hours later with crystal violet. (b) MDBK (bovine kidney) cell line was seeded simultaneously with 2-fold dilutions of samples. Vesicular stomatitis virus was added after 2 to 3 hours incubation and plates were stained with crystal violet 16 to 18 hours later. To test pH 2 stability bacterial extracts and standards were diluted in minimal essential medium to a concentration of 1000 units/ml. One ml aliquots were adjusted to pH 2 with 1N HCl, incubated at 4° C. for 16 hours, and neutralized by addition of NaOH. IF activity was determined by the CPE inhibition assay using human amnion cells. To establish antigenic identity 25 μl aliquots of the 1000 U/ml interferon samples (untreated) were incubated with 25 μl of rabbit antihuman leukocyte interferon for 60' at 37° C., centrifuged at 12,000× g for 5 minutes and the supernatant assayed. Fibroblast and leukocyte interferon standards were obtained from the National Institutes of Health. Rabbit antihuman leukocyte interferon was obtained from the National Institute of Allergy and Infectious Diseases.

RESULTS

Chemical synthesis of primer pools complementary of FIF mRNA.

The amino-terminal protein sequence of human fibroblast interferon (4) permitted us to deduce the 24 possible mRNA sequences which could code for the first four amino acids. The 24 complementary deoxyoligonucleotides were synthesized in 6 pools of 4 dodecamers each (FIG. 1).

The six pools of 4 deoxyoligonucleotides each were synthesized by a modified phosphotriester method that has been used previously for the rapid synthesis of oligonucleotides in solution (12) and on solid phase (14). The basic strategy involved reacting two different 3'-blocked trimers with an excess of a single 5'-protected trimer to yield a pool of two hexamers, each represented equally. The coupling of two pools, each containing two hexamers, then resulted in a pool of four dodecamers.

Identification of FIF cDNA clones.

Using 12S mRNA from induced human fibroblasts (1,000 units IF activity per μg in oocyte assay), double stranded cDNA was prepared and inserted into pBR322 at the Pst I site by the standard dG:dC tailing method (20). A fibroblast cDNA library consisting of 30,000 ampicillin-sensitive, tetracycline-resistant transformants of E. coli K-12 strain 294 was obtained from 20 ng of cDNA ranging in size from 550 to 1300 base pairs. Plasmid DNA was prepared from 600 of the transformants and applied to 3 sets of nitrocellulose filters as described in Materials and Methods.

The approach followed in the identification of hybrid plasmids containing fibroblast interferon cDNA sequences was similar to that used to identify human leukocyte interferon recombinant plasmids (30). Radiolabeled cDNA hybridization probes were prepared using either the 24 synthetic dodecamers or oligo(dT)$_{12-18}$ as primers and 12S RNA from induced fibroblasts (5000 units/μg in oocytes) as template. The $^{32}$P-cDNAs (specific activity >5×10$^8$ cpm/μg) obtained were hybridized to a large excess of mRNA isolated from uninduced human fibroblasts, and the mRNA-cDNA hybrids were separated from unreacted cDNA by hydroxyapatite chromatography (24). The single stranded cDNA fractions should be enriched for sequences which are present in induced fibroblasts but absent in uninduced cells, and the mRNA-cDNA hybrids should represent sequences common to both induced and uninduced cells. Approximately 4×10$^6$ cpm of single stranded cDNA (hybridization probe A) and 8×10$^6$ cpm of cDNA-mRNA hybrids were obtained using oligo(dT)$_{12-18}$ primed cDNA; 1.5×10$^6$ cpm of single stranded (hybridization probe B) and 1.5×10$^5$ cpm of hybrids were obtained from cDNA primed using synthetic dodecamer pools Fib 1–6. The cDNA-mRNA hybrids from both fractionations were combined, the RNA hydrolyzed by treatment with alkali, and the $^{32}$P-cDNA used as hybridization probe C. Many of the 600 plasmid samples hybridized with both probes A and C, indicating that the hybridization reactions between uninduced mRNA and $^{32}$P-cDNA (prior to the hydroxyapatite fractionation step) had not gone to completion. However, only one of the 600 plasmids (pF526) hybridized strongly with the specifically primed, induced cDNA probe B (FIG. 2). Plasmid pF526 also hybridized with the total oligo(dT)$_{12-18}$ primed, induced cDNA probe A, and failed to give detectable hybridization to the combined uninduced probe C.

Pst I digestion of pF526 showed the cloned cDNA insert to be about 550 base pairs long, probably too short to contain the entire coding region for a protein the size of fibroblast interferon. Therefore, a $^{32}$P-labeled DNA probe was prepared from this Pst I fragment by random priming with calf thymus DNA (10). This probe was used to screen 2000 individual colonies from a newly constructed fibroblast cDNA library (the new cDNA library was prepared using 12S mRNA from induced fibroblasts having a titer of 6,000 units/ml in the oocyte assay system). Sixteen clones hybridized to the probe. Plasmids prepared from the majority of these released two fragments when cleaved with Pst I, indicating that the cDNA contained an internal Pst I site. Clone pFIF3 contained the largest cDNA insert, about 800 base pairs. The DNA sequence of the insert was determined by the Maxam-Gilbert procedure (9) and is shown in FIG. 3. The amino acid sequence of human fibroblast interferon predicted from the nucleotide sequence is identical to that reported recently by Taniguchi et al. (31) and by Derynck et al. (7) from DNA sequencing of FIF cDNA clones. A precursor or signal peptide of 21 amino acids is followed by a mature interferon polypeptide of 166 amino acids, a stretch of 196 3'-untranslated nucleotides and a poly(A) tail. The $NH_2$-terminal 20 amino acids of mature FIF have been directly determined by protein microsequencing and are the same as those predicted from the DNA sequence. The calculated formula molecular weight of mature human fibroblast interferon having the 166 amino acids shown in FIG. 3 is about 20,027.

Direct expression of fibroblast interferon.

To express high levels of mature fibroblast interferon in *E. coli*, initiation of protein synthesis must occur at the ATG codon of the mature polypeptide (amino acid 1) rather than at the ATG of the signal peptide (amino acid S1) (FIG. 3).

Figure 5:
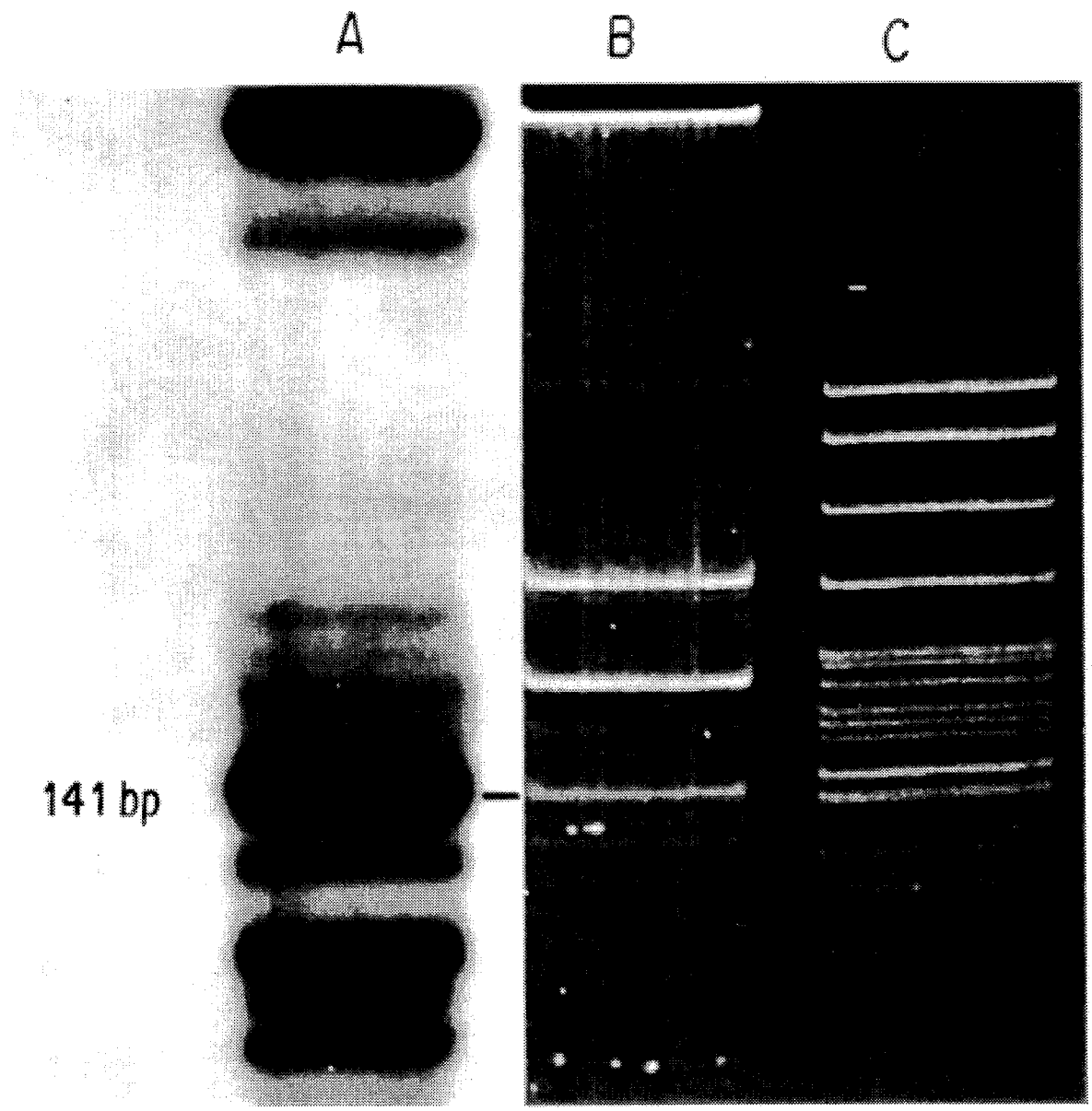
FIG. 5 is an autoradiograph of the polyacrylamide gel used to isolate the 141bp fragment lacking the signal peptide coding regions.

Our approach to removing the signal peptide coding regions from pFIF3 is depicted in FIG. 4. A 1200 bp DNA fragment which contained the entire cDNA insert was isolated from a polyacrylamide gel after digesting pFIF3 with Hha I. Two separate synthetic deoxyoligonucleotide primers, dATGAGCTACAAC(I) and dCATGAGCTACAAC(II), were prepared. Both primers contain the coding sequence for the first four amino acids of mature fibroblast interferon; primer II has an additional C at the 5'-terminus. Primer repair reactions and subsequent ligations were carried out separately for primers I and II, and gave nearly identical results. Therefore, only reactions using primer I are discussed in detail here. The primers were 5'-radiolabeled using ($\gamma$-$^{32}$P)ATP and T4 polynucleotide kinase, combined with the 1200 bp Hha I DNA fragment and the mixture denatured by boiling. Following hybridization of the primer to the denatured Hha I DNA fragment, *E. coli* DNA polymerase I Klenow fragment (33) was used to catalyze the repair synthesis of the plus (top) strand (FIG. 4). In addition, the associated 3'$\geq$5' exonuclease activity of the Klenow fragment removed the 3'-protruding end from the minus (bottom) strand, leaving a flush end. Analysis of samples of the reaction mixture by polyacrylamide gel electrophoresis indicated that the repair synthesis did not go to completion, but stopped at several discrete sites. Therefore, the entire reaction mixture was treated with Pst I and the desired 141 bp fragment (180,000 Cerenkov cpm; ~0.3 pmole) was purified by polyacrylamide gel electrophoresis (FIG. 5). Ligation of this fragment to 1 µg (~4 pmole) of the 363 bp Pst I-Bgl II fragment isolated from pFIF3 (FIG. 4), followed by Bgl II digestion, yielded 50,000 Cerenkov cpm (~0.1 pmole, ~30 ng) of the 504 bp DNA fragment containing the entire coding sequence for mature fibroblast interferon. The same reactions using primer II gave 83,000 cpm (~0.15 pmole, ~50 ng) of 505 bp product.

Figure 6:
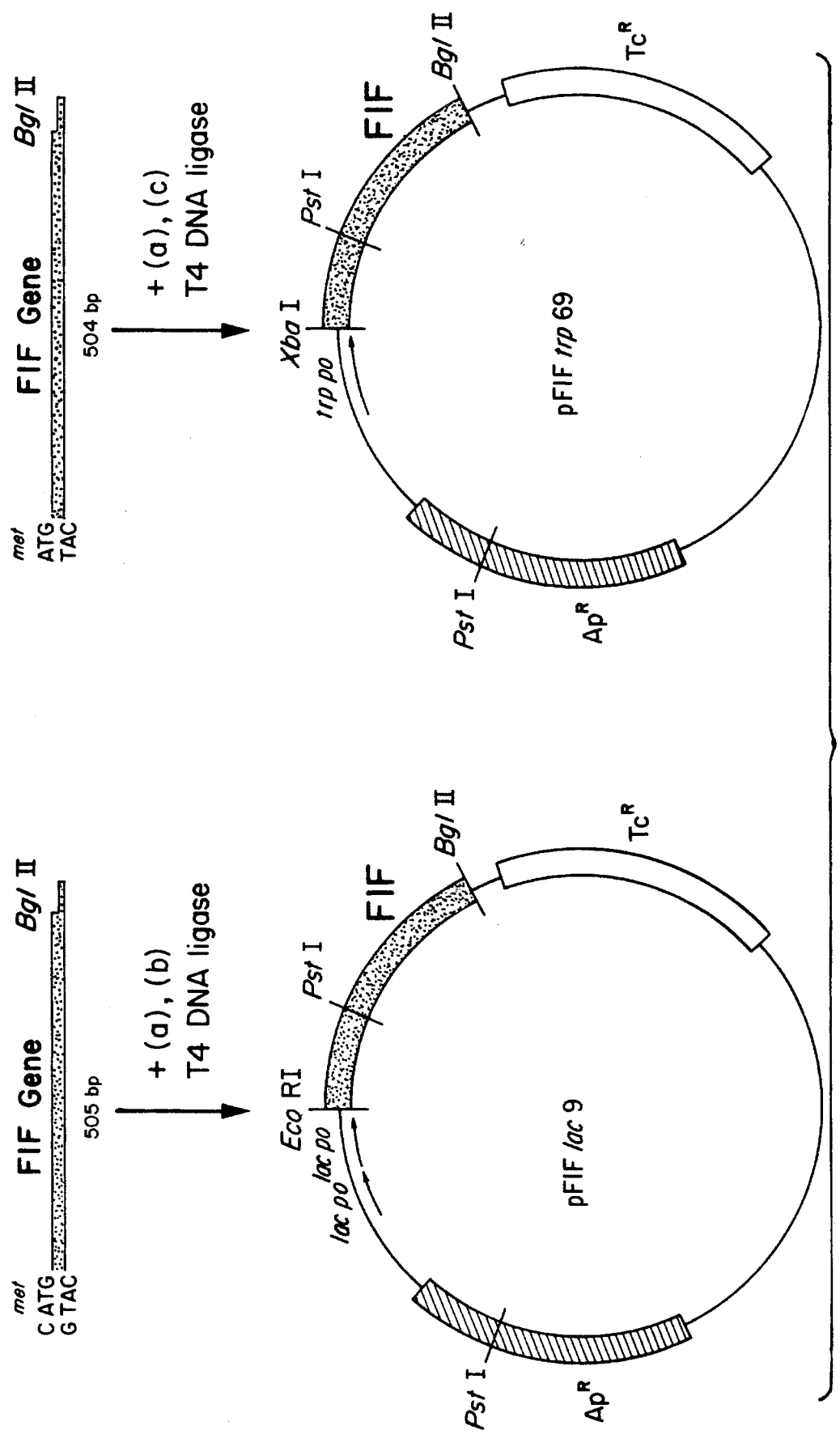

The construction of plasmids which direct the synthesis of human fibroblast interferon is outlined in FIG. 6. Separate expression plasmids were constructed which placed FIF synthesis under the control of the *E. coli* lac or trp promoter-operator systems. Both of these systems have proven useful for the direct expression of eukaryotic genes in *E. coli*: human growth hormone has been efficiently synthesized using the lac system (21) and human leukocyte interferon has been produced at high levels using the trp system (30) and *Nature* 287, 411 (1980).

pBRH trp was digested with EcoRI restriction enzyme and the resulting fragment isolated by PAGE and electroelution. EcoRI-digested plasmid pSom 11 (K. Itakura et al., *Science* 198, 1056 (1977); G.B. patent publication no. 2 007 676 A) was combined with the above fragment. The mixture was ligated with T$_4$ DNA ligase as previously described and the resulting DNA transformed into *E. coli* K-12 strain 294 as previously described. Transformant bacteria were selected on ampicillin-containing plates. Resulting ampicillin-resistant colonies were screened by colony hybridization (M. Gruenstein et al., Proc Nat'l Acad Sci USA 72, 3951–3965 [1975]) using as a probe the trp promoter-operator-containing the above fragment isolated from pBRHtrp, which had been radioactively labelled with p$^{32}$. Several colonies shown positive by colony hybridization were selected, plasmid DNA was isolated and the orientation of the inserted fragments determined by restriction analysis employing restriction enzymes BglII and BamHI in double digestion. *E. coli* 294 containing the plasmid designated pSOM7$\Delta$2, which has the trp promoter-operator fragment in the desired orientation was grown in LB medium containing 10 µg/ml ampicillin. The cells were grown to optical density 1 (at 550 nM), collected by centrifugation and resuspended in M9 media in tenfold dilution. Cells were grown for 2–3 hours, again to optical density 1, then lysed and total cellular protein analyzed by SDS (sodium dodecyl sulfate) urea (15 percent) polyacrylamide gel electrophoresis (J. V. Maizel Jr. et al., Meth Viral 5, 180–246 [1971]).

Plasmid pBR322 was Hind III digested and the protruding Hind III ends in turn digested with S1 nuclease. The S1 nuclease digestion involved treatment of 10 µg of Hind III-cleaved pBR322 in 30 µl S1 buffer (0.3M NaCl, 1 mM ZnCl$_2$, 25 mM sodium acetate, pH 4.5) with 300 units S1 nuclease for 30 minutes at 15° C. The reaction was stopped by the addition of 1 µl of 30×S1 nuclease stop solution (0.8M tris base, 50 mM EDTA). The mixture was phenol extracted, chloroform extracted and ethanol precipitated, then EcoRI digested as previously described and the large fragment (1) obtained by PAGE procedure followed by electroelution. The fragment obtained has a first EcoRI sticky end and a second, blunt end whose coding strand begins with the nucleotide thymidine.

Plasmid pSom7 $\Delta$2, as prepared above, was Bgl II digested and the Bgl II sticky ends resulting made double stranded with the Klenow polymerase I procedure using all four deoxynucleotide triphosphates. EcoRI cleavage of the resulting product followed by PAGE and electroelution of the small fragment (2) yielded a linear piece of DNA containing the tryptophan promoter-operator and codons of the LE' "Proximal" sequence upstream from the Bgl II site ("LE'(p)"). The product had an EcoRI end and a blunt end resulting from filling in the Bgl II site. However, the Bgl II site is reconstituted by ligation of the blunt end of the above fragment (2) to the blunt end of the above prepared fragment (1). Thus, the two fragments were ligated in the presence of T$_4$ DNA ligase to form the recirculated plasmid pHKY 10 which was propagated by transformation into competent *E. coli* strain 294 cells.

Plasmid pGM1 carries the *E. coli* tryptophan operon containing the deletion $\Delta$LE1413 (G. F. Miozzari, et al., (1978) *J. Bacteriology* 133, 1457–1466)) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. The plasmid, 20 µg, was digested with the restriction enzyme PvuII which cleaves the plasmid at five sites. The gene fragments were next combined with EcoRI linkers (consisting of a self complementary oligonucleotide of the sequence: pCAT-GAATTCATG) providing an EcoRI cleavage site for a later cloning into a plasmid containing an EcoRI site. The 20 µg of DNA fragments obtained from pGM1 were treated with 10 units T$_4$ DNA ligase in the presence of 200 pico moles of the 5'-phosphorylated synthetic oligonucleotide pCAT-GAATCATG and in 20 µl T$_4$ DNA ligase buffer (20 mM tris, pH 7.6, 0.5 mM ATP, 10 mM MgCl$_2$, 5 mM dithiothreitol) at 4° C. overnight. The solution was then heated 10 minutes at 70° C. to halt ligation. The linkers were cleaved by EcoRI digestion and the fragments, now with EcoRI ends were separated using 5 percent polyacrylamide gel electrophoresis (hereinafter "PAGE") and the three largest fragments isolated from the gel by first staining with ethidium bromide, locating the fragments with ultraviolet light, and cutting from the gel the portions of interest. Each gel fragment, with 300 microliters 0.1×TBE, was placed in a dialysis bag and subjected to electrophoresis at 100 v for one hour in 0.1× TBE buffer (TBE buffer contains: 10.8 gm tris base, 5.5 gm boric acid, 0.09 gm Na$_2$EDTA in 1 liter H$_2$O). The aqueous solution was collected from the dialysis bag, phenol extracted, chloroform extracted and made 0.2M sodium chloride, and the DNA recovered in water after ethanol precipitation. The trp promoter-operator-containing gene with EcoRI sticky ends was identified in the procedure next described, which entails the insertion of fragments into a tetracycline sensitive plasmid which, upon promoter-operator insertion, becomes tetracycline resistant.

Plasmid pBRH1 (R. I. Rodriguez, et al, Nucleic Acids Research 6, 3267–3287 [1979]) expresses ampicilin resistance and contains the gene for tetracycline resistance but, there being no associated promoter, does not express that resistance. The plasmid is accordingly tetracycline sensitive. By introducing a promoter-operator system in the EcoRI site, the plasmid can be made tetracycline resistant.

pBRH1 was digested with EcoRI and the enzyme removed by phenol extraction followed by chloroform extraction and recovered in water after ethanol precipitation. The resulting DNA molecule was, in separate reaction mixtures, combined with each of the three DNA fragments obtained above and ligated with T$_4$ DNA ligase as previously described. The DNA present in the reaction mixture was used to transform competent *E. coli* K-12 strain 294, K. Backman et al., Proc Nat'l Acad Sci USA 73, 4174–4198 [1976]) by standard techniques (V. Hershfield et al., Proc Nat'l Acad Sci USA 71, 3455–3459 [1974]) and the bacteria plated on LB plates containing 20 μg/ml ampicillin and 5 μg/ml tetracycline. Several tectracycline-resistant colonies were selected, plasmid DNA isolated and the presence of the desired fragment confirmed by restriction enzyme analysis. The resulting plasmid is designated pBRHtrp.

An EcoRI and BamHI digestion product of the viral genome of hepatitis B was obtained by conventional means and cloned into the EcoRI and BamHI sites of plasmid pGH6 (D. V. Goeddel et al., Nature 281, 544 [1979])) to form the plasmid pHS32. Plasmid pHS32 was cleaved with XbaI, phenol extracted, chloroform extracted and ethanol precipitated. It was then treated with 1 μl *E. coli* polymerase I, Klenow fragment (Boehringer-Mannheim) in 30 μl polymerase buffer (50 mM potassium phosphate pH 7.4, 7 mM MgCl$_2$, 1 mM β-mercaptoethanol) containing 0.1 mM dTTP and 0.1 mM dCTP for 30 minutes at 0° C. then 2 hr. at 37° C. This treatment causes 2 of the 4 nucleotides complementary to the 5' protruding end of the XbaI cleavage site to be filled in: t,0170

Two nucleotides, dC and dT, were incorporated giving an end with two 5' protruding nucleotides. This linear residue of plasmid pHS32 (after phenol and chloroform extraction and recovery in water after ethanol precipitation) was cleaved with EcoRI. The large plasmid fragment was separated from the smaller EcoRI-XbaI fragment by PAGE and isolated after electroelution. This DNA fragment from pHS32 (0.2 μg), was ligated, under conditions similar to those described above, to the EcoRI-Taq I fragment of the tryptophan operon (~0.01 μg), derived from pBRHtrp.

In the process of ligating the fragment from pHS32 to the Eco RI-Taq I fragment, as described above, the Taq I protruding end is ligated to the XbaI remaining protruding end even though it is not completely Watson-Crick base-paired: t,0180

A portion of this ligation reaction mixture was transformed into *E. coli* 294 cells, heat treated and plated on LB plates containing ampicillin. Twenty-four colonies were selected, grown in 3 ml LB media, and plasmid isolated. Six of these were found to have XbaI site regenerated via E. coli catalyzed DNA repair and replication: t,0181

These plasmids were also found to cleave both with EcoRI and HpaI and to give the expected restriction fragments. One plasmid, designated pTrp 14, was used for expression of heterologous polypeptides, as next discussed.

The plasmid pHGH 107 (D. V. Goeddel et al, Nature, 281, 544, 1979) contains a gene for human growth hormone made up of 23 amino acid codons produced from synthetic DNA fragments and 163 amino acid codons obtained from complementary DNA produced via reverse transcription of human growth hormone messenger RNA. This gene, though it lacks the codons of the "pre" sequence of human growth hormone, does contain an ATG translation initiation codon. The gene was isolated from 10 μg pHGH 107 after treatment with EcoRI followed by *E. coli* polymerase I Klenow fragment and dTTP and dATP as described above. Following phenol and chloroform extraction and ethanol precipitation the plasmid was treated with BamHI.

The human growth hormone ("HGH") gene-containing fragment was isolated by PAGE followed by electroelution. The resulting DNA fragment also contains the first 350 nucleotides of the tetracycline resistance structural gene, but lacks the tetracycline promoter-operator system so that, when subsequently cloned into an expression plasmid, plasmids containing the insert can be located by the restoration of tetracycline resistance. Because the EcoRI end of the fragment has been filled in by the Klenow polymerase I procedure, the fragment has one blunt and one sticky end, ensuring proper orientation when later inserted into an expression plasmid.

The expression plasmid pTrp14 was next prepared to receive the HGH gene-containing fragment prepared above. Thus, pTrp14 was XbaI digest and the resulting sticky ends filled in with the Klenow polymerase I procedure employing dATP, dTTP, dGTP and dCTP. After phenol and chloroform extraction and ethanol precipitation the resulting DNA was treated with BamHI and the resulting large plasmid fragment isolated by PAGE and electroelution. The pTrp14-derived fragment had one blunt and one sticky end, permitting recombination in proper orientation with the HGH gene containing fragment previously described.

The HGH gene fragment and the pTrp14 ΔXba-BamHI fragment were combined and ligated together under conditions similar to those described above. The filled in XbaI and EcoRI ends ligated together by blunt end ligation to recreate both the XbaI and the EcoRI site: t,0190

This construction also recreates the tetracycline resistance gene. Since the plasmid pHGH 107 expresses tetracycline resistance from a promoter lying upstream from the HGH gene (the lac promoter), this construction, designated pHGH 207, permits expression of the gene for tetracycline resistance under the control of the tryptophan promoter-operator. Thus the ligation mixture was transformed into *E. coli* 294 and colonies selected on LB plates containing 5 μg/ml tetracycline.

Plasmid pHGH 207 was EcoRI digested and the trp promoter containing EcoRI fragment recovered by PAGE followed by electroelution. Plasmid pBRH1 was EcoRI digested and the cleaved ends treated with bacterial alkaline phosphatase ("BAP") (1 μg, in 50 mM tris pH 8 and 10 mM MgCl$_2$ for 30 min. at 65° C.) to remove the phosphate groups on the protruding EcoRI ends. Excess bacterial alkaline phosphatase was removed by phenol extraction, chloroform extraction and ethanol precipitation. The resulting linear DNA, because it lacks phosphates on the protruding ends thereof, will in ligation accept only inserts whose complementary stick ends are phosphorylated but will not itself recircularize, permitting more facile screening for plasmids containing the inserts.

The EcoRI fragment derived from pHGH 207 and the linear DNA obtained from pBRH1 were combined in the presence of $T_4$ ligase as previously described and ligated. A portion of the resulting mixture was transformed into E. coli strain 294 as previously described, plated on LB media containing 5 μg/ml of tetracycline, and 12 tetracycline resistant colonies selected. Plasmid was isolated from each colony and examined for the presence of a DNA insert by restriction endonuclease analysis employing EcoRI and XbaI. One plasmid containing the insert was designated pHKY1.

The plasmid pHKY10, described above, is a derivative of pBR322 which contains a Bgl II site between the tetracycline resistance ($Tc^R$) promoter and structural gene (32). The large DNA fragment isolated after digesting pHKY10 with Pst I and Bgl II therefore contains part of the ampicillin resistance ($Ap^R$) gene and all of the $Tc^R$ structural gene, but lacks the $Tc^R$ promoter (FIG. 6). The plasmid pGH6 (21) was digested with Eco RI, the resulting single stranded ends were filled in with DNA polymerase I, and the plasmid was cleaved with Pst I. The small fragment, containing part of the $Ap^R$ gene, a double lac promoter and lac ribosome binding site, but lacking an ATG initiation triplet was isolated. A similar trp promoter fragment, containing the trp leader ribosome binding site, but lacking an ATG sequence (30), may be isolated from pHKY1 described above; see (32) (see FIG. 6).

The trp fragment just referred to is an analog of the E. coli tryptophan operon from which the so-called trp attenuator has been deleted, See J. Bact. 133, 1457 (1978), to controllably heighten expression levels. Expression plasmids containing the modified trp regulon can be grown to predetermined levels in nutrient media containing additive tryptophan in quantities sufficient to repress the promoter-operator system, then be deprived of tryptophan so as to derepress the system and occasion the expression of the intended product.

The expression plasmids may be assembled via three part ligation reactions as shown in FIG. 6. 15 ng (~0.05 pmole) of the assembled FIF gene (504 or 505 bp), 0.5 μg (~0.2 pmole) of the large Pst I-Bgl II fragment of pHKY10 and 0.2 μg (~0.3 pmole) of the appropriate promoter fragment were ligated and the mixture used to transform E. coli 294 (22). Plasmid DNA was prepared from individual transformants and analyzed by restriction mapping. Correct joining of the assembled gene to the promoter fragment should restore the Eco RI (lac) or the Xba I (trp) recognition sequences. The majority of the plasmids gave the expected restriction enzyme digestion patterns. Individual clones (12 containing the trp promoter and 12 containing the lac promoter) were grown and extracts prepared for interferon assay as described in Materials and Methods.

When assayed on human amnion (WISH) cells for antiviral activity by the CPE inhibition assay (1) five of the trp transformants were positive (each approximately equivalent); eleven of the lac transformants gave equivalent IF activities. Therefore, one transformant from each series (pFIFlac9 and pFIFtrp69) was selected for further study (Table 1). DNA sequence analysis demonstrated that the desired attachment of promoter to FIF structural gene had occurred in both cases. t,0210

The amounts of fibroblast interferon produced by pFIFlac9 and pFIFtrp69 are shown in Table 1. The trp promoter gave a FIF expression level measurably higher than did the lac promoter. In an attempt to further increase FIF expression levels, pFIFtrp69 was cleaved with Eco RI and two 300 base pair Eco RI fragments containing the trp promoter (30) were inserted. The resulting plasmid, pFIFtrp$^3$69, contains three successive trp promoters which read toward the FIF gene. The amount of FIF synthesized by E. coli K-12 strain 294/pFIF trp$^3$69 is 4–5 times that produced by pFIF trp 69 (Table 1). This is apparently due to the derepression of the trp promoter which occurs when trp repressor levels are titrated by the multiple copies of the trp operator.

The FIF produced by E. coli K-12 strain 294/pFIFtrp69 behaves like authentic human FIF. As shown in Table 2, its antiviral activity is about 30 times greater on human cells than bovine cells. In addition, the bacterially produced FIF is stable to treatment at pH 2 overnight and is not neutralized by rabbit antihuman leukocyte interferon antibodies (Table 3). t,0220 t,0221

Purification

The purification procedure for bacterial derived fibroblast is as follows:

1. Frozen cells are suspended in twelve times volume per weight with sucrose lysis buffer (100 mM Tris-HCl, 10 percent sucrose, 0.2M NaCl, 50 mM EDTA, 0.2 mM PMSF, pH 7.9) containing lysozyme at 1 mg ml$^{-1}$. The cell suspension is stirred for 1 hour at 4° C. and centrifuged. Fibroblast interferon activity remains in the supernatant.

2. Polyethyleneimine (5 percent v/v) is added to the sonicated supernatant to a final concentration of 0.5 percent (v/v). The solution is stirred for 1 hour at 4° C. and centrifuged. Interferon activity remains in the supernatant.

3. Solid ammonium sulfate is added to the polyethyleneimine supernatant to a final concentration of 50 percent saturation, stirred for 30 minutes at 4° C. and centrifuged. Interferon activity is in the 50 percent pellet.

4. The 50 percent ammonium sulfate pellet is suspended in one half the volume of the 50 percent ammonium sulfate suspension with Phosphate Buffered Saline (20 mM sodium phosphate 0.15M NaCl, pH 7.4). Polyethylene glycol 6000 (50 percent w/v in PBS) is added to a final concentration of 12½ percent (v/v), stirred at 4° C. for 2 hours and centrifuged. Interferon activity is in the pellet. The pellet is suspended in a minimal volume of sucrose lysis buffer and clarified by centrifugation.

This initial extraction procedure results in a purification of fibroblast interferon from 0.001 percent of the total protein to 0.05 percent of the total protein. This material can be further purified to homogeneity by the following column chromatography steps:

5. Afinity chromatography on Amicon Blue B in sucrose lysis buffer.
6. Anion exchange chromatography on QAE Sephadex in sucrose lysis buffer in the absence of 0.2M NaCl.
7. Size exclusion chromatography on Sephadex G-75 in sucrose lysis buffer.
8. Reverse phase high pressure liquid chromatography.

Parenteral Administration

FIF may be parenterally administered to subjects requiring antitumor or antiviral treatment. Dosage and dose rate may parallel that currently in use in clinical investigations of human derived materials, e.g., about $(1-10) \times 10^6$ units daily, and in the case of materials of purity greater than 1 percentage, likely up to, e.g., 150×10⁶ units daily. Dosages of bacterially obtained FIF could be significantly elevated for greater effect owning to the essential absence of human proteins other than FIF, which proteins in fibroblast-derived materials may act as pyrogens, exhibiting adverse effects, e.g., malaise, temperature elevation, etc.

As one example of an appropriate dosage form for essentially homogeneous bacterial FIF in parenteral form, 3 mg. FIF of specific activity of, say, 2×10⁸ µ/mg may be dissolved in 25 ml. 5 percentage serum albumin (human) - USP, the solution passed through a bacteriological filter and the filtered solution aspetically subdivided into 100 vials, each containing 6×10⁶ units pure interferon suitable for parenteral administration. The vials are preferably stored in the cold (–20° C.) prior to use.

The compounds of the present invention can be formulated according to known methods to prepare pharmaceutically useful compositions, whereby the polypeptide hereof is combined in admixture with a pharmaceutically acceptable carrier vehicle. Suitable vehicles and their formulation are described in Remington's *Pharmaceutical Sciences* by E. W. Martin, which is hereby incorporated by reference. Such compositions will contain an effective amount of the interferon protein hereof together with a suitable amount of vehicle in order to prepare pharmaceutically acceptable compositions suitable for effective administration to the host. One preferred mode of administration is parenteral.

BIBLIOGRAPHY

1. Stewart, W. E. II (1979) The Interferon System, Springer, N.Y.
2. Knight, E. Jr. (1976) Proc. Natl. Acad. Sci. U.S.A. 73, 520–523.
3. Berthold, W., Tan, C., and Tan, Y. H. (1978) J. Biol. Chem. 253, 5206–5212.
4. Knight, E. Jr., Hunkapillar, M. W., Korant, B. D., Hardy, R. W. F. and Hood, L. E. (1980) Science 207, 525–526.
5. Houghton, M., Stewart, A. G., Doel, S. M., Emtage, J. S., Eaton, M. A. W., Smith, J. C., Patel, T. P., Lewis, H. M., Porter, A. G., Birch, J. R., Cartwright, T., and Carey, N. H. (1980) Nucleic Acids Res. 8, 1913–1931.
6. Taniguchi, T., Sakai, M., Fujii-Kuriyama, Y., Muramatsu, M., Kobayashi, S., and Sudo, T. (1979) Proc. Jan Acad. B55, 464–469.
7. Derynck, R., Content, J., DeClercq, E., Volckaert, G., Tavernier, J., Devos, R., and Fiers, W. (1980) Nature 285, 542–547.
8. Clewell, D. B. (1972) J. Bacteriol. 110, 667–676.
9. Maxam, A. M. and Gilbert, W. (1980) Methods Enzymol. 65, 499–560.
10. Taylor, J. M., Illemensee, R. and Summer, S. (1976) Biochim. Biophys. Acta 442, 324–330.
11. Grunstein, M. and Hogness, D. S. (1975) Proc. Natl. Acad. Sci. U.S.A. 72, 3961–3965.
12. Crea, R., Kraszewski, A., Hirose, T. and Itakura, K. (1978) Proc. Natl. Acad. Sci. U.S.A. 75, 5765–5769.
13. Hirose, T., Crea, R. and Itakura, K. (1978) Tetrahedron Letters 28, 2449–2452.
14. Crea, R. and Horn, T. (1980) Nucleic Acids Res. 8, 2331–2348.
15. Pestka, S., McInnes, J., Havell, E. A. and Vilcek, J. (1975) Proc. Natl. Acad. Sci. U.S.A. 72, 3898–3901.
16. Green, M., Zehavi-Willner, T., Graves, P. N., McInnes, J. and Pestka, S. (1975) Arch. Biochem. Biophys. 172, 74–89.
17. Gurdon, J. B., Lane, C. D., Woodland, H. R. and Marbaix, G. (1971) Nature 233, 177–182.
18. Cavalieri, R. L., Havell, E. A. Vilcek, J. and Pestka, S. (1977) Proc. Natl. Acad. Sci. U.S.A. 74, 3287–3291.
19. Scheller, R. H., Dickerson, R. E., Boyer, H. W., Riggs, A. D. and Itakura, K. (1977) Science 196, 177–180.
20. Chang, A. C. Y., Nunberg, J. H., Kaufman, R. J. Erlich, H. A., Schimke, R. T. and Cohen, S. N. (1978) Nature 275, 617–624.
21. Goeddel, D. V., Heyneker, H. L., Hozumi, T., Arentzen, R., Itakura, K., Yansura, D. G., Ross, M. J., Miozzari, G., Crea, R. and Seeburg, P. H. (1979) Nature 281, 544–548.
22. Backman, K., Ptashne, M. and Gilbert, W., (1976) Proc. Natl. Acad. Sci. U.S.A. 73, 4174–4178.
23. Hershfield, V., Boyer, H. W., Yanofsky, C., Lovett, M. A. and Helinski, D. R. (1974) Proc. Natl. Acad. Sci. U.S.A. 71, 3455–3459.
24. Galau, G. A., Britten, R. J. and Davidson, E. H. (1977) Proc. Natl. Acad. Sci. U.S.A. 74, 1020–1023.
25. Birnboim, H. C. and Doly, J. (1979) Nucleic Acid Res. 7, 1513–1523.
26. Kafatos, F. C., Jones, C. W. and Efstratiadis, A. (1979) Nucleic Acids Res. 7, 1541–1552.
27. Denhardt, D. T. (1966) Biochem. Biophys. Res. Comm. 23,641.
28. Goeddel, D. V., Kleid, D. G., Bolivar, F., Heyneker, H. L., Yansura, D. G., Crea, R., Hirose, T., Kraszewski, A., Itakura, K. and Riggs, A. D. (1979) Proc. Natl. Acad. Sci. U.S.A. 76, 106–110.
29. Miller, J. H. (1972) Experiments in Molecular Genetics, pp.431–433, Cold Spring Harbor Laboratory, Cold Spring Harbor, N.Y.
30. U.S. patent application of David V. Goeddel and Sidney Pestka U.S. Ser. No. 184909, filed Sep. 8, 1980 for Microbial Production of Mature Human Leukocyte Interferon, Attorney docket 1980/104, assigns Genentech, Inc. and Hoffmann-LaRoche, Inc.
31. Taniguchi, T., Ohno, S., Fujii-Kuriyama, Y. and Muramatsu, M. (1980) Gene 10, 11–15.
32. U.S. patent application Ser. No. 06/133,296 filed Mar. 24, 1980 by Dennis G. Kleid et al., assigned to Genentech, Inc.
33. Klenow, H. and Henningsen, I. (1970) Proc. Natl. Acad. Sci. U.S.A. 65, 168–171.

We claim:

1. A composition comprising water and a nonglycosylated polypeptide having the amino acid sequence of a mature human fibroblast interferon, said nonglycosylated polypeptide having a total of 165 or 166 amino acids and said composition being free of any glycosylated human fibroblast interferon.

2. The composition of claim 1, said nonglycosylated polypeptide having the amino acid sequence X-Ser-Tyr-Asn-Leu-Leu-Gly-Phe-Leu-Gln-Arg-Ser-Ser-Asn-Phe-Gln-Cys-Gln-Lys-Leu-Leu-Trp-Gln-Leu-Asn-Gly-Arg-Leu-Glu-Tyr-Cys-Leu-Lys-Asp-Arg-Met-Asn-Phe-Asp-Ile-Pro-Glu-Glu-Ile-Lys-Gln-Leu-Gln-Gln-Phe-Gln-Lys-Glu-Asp-Ala-Ala-Leu-Thr-Ile-Tyr-Glu-Met-Leu-Gln-Asn-Ile-Phe-Ala-Ile-Phe-Arg-Gln-Asp-Ser-Ser-Ser-Thr-Gly-Trp-Asn-Glu-Thr-Ile-Val-Glu-Asn-Leu-Leu-Ala-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Arg-Ile-Leu-His-Tyr-Leu-Lys-Ala-Lys-Glu-Tyr-Ser-His-Cys-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn, wherein X is H or Met.

3. The composition of claim 2, said nonglycosylated polypeptide having a formula molecular weight of about 20,027.

4. The composition of claim 1, 2 or 3, said composition being free of human proteins.

5. The composition of claim 1, 2 or 3, said composition containing a therapeutically effective amount of said nonglycosylated polypeptide and being suitable for parenteral administration.

6. The composition of claim 4, said composition containing a therapeutically effective amount of said nonglycosylated polypeptide and being suitable for parenteral administration.

* * * * *

UNITED STATES PATENT AND TRADEMARK OFFICE
CERTIFICATE OF CORRECTION

PATENT NO. : 5,460,811

DATED : October 24, 1995

INVENTOR(S) : David V. Goeddel and Roberto Crea

It is certified that error appears in the above-identified patent and that said Letters Patent is hereby corrected as shown below:

In column 5, line 663, please delete ($\alpha^{32}$p)dCTP and insert ($\alpha^{32}$P)dCTP.

In column 7, line 16, please delete 500 and insert 550.

In column 10, line 61, please delete GAATCATG and insert GAATTCATG.

In column 11, line 52, please delete t,0170 and insert

| | | | |
|---|---|---|---|
| 5' | CTAGA— | 5' | CTAGA— |
| 3' | T— | 3' | TCT— |

UNITED STATES PATENT AND TRADEMARK OFFICE
CERTIFICATE OF CORRECTION

PATENT NO. : 5,460,811

DATED : October 24, 1995

INVENTOR(S) : David V. Goeddel and Roberto Crea

Page 2 of 6

In column 11, line 67, please delete t.0180 and insert

```
—T              CTAGA—           —TCTAGA—
         +                  ⟶
—AGC            TCT—             —AGCTCT—
```

In column 12, line 6, please delete t.0181 and insert

```
—TCTAGA—                    —TCTAGA—
              ⟶
—AGCTCT—                    —AGATCT—
```

UNITED STATES PATENT AND TRADEMARK OFFICE
CERTIFICATE OF CORRECTION

PATENT NO. : 5,460,811

DATED : October 24, 1995

INVENTOR(S) : David V. Goeddel and Roberto Crea

In column 12, line 51, please delete t,0190 and insert

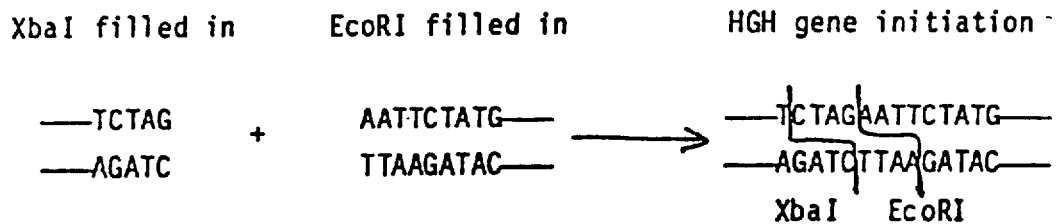

UNITED STATES PATENT AND TRADEMARK OFFICE
CERTIFICATE OF CORRECTION

PATENT NO. : 5,460,811

DATED : October 24, 1995

INVENTOR(S) : David V. Goeddel and Roberto Crea

In column 13, line 67, please delete t,0210 and insert

Table 1.  Interferon activity in extracts of E. coli

| E. coli K-12 strain 294 transformed by: | Cell density (cells/ml) | IF Activity (units/l culture) | FIF molecules per cell |
|---|---|---|---|
| pBR322 | $3.5 \times 10^8$ | - | - |
| pFIFlac9 | $3.5 \times 10^8$ | $9.0 \times 10^6$ | 2,250 |
| pFIFtrp69 | $3.5 \times 10^8$ | $1.8 \times 10^7$ | 4,500 |
| pFIFtrp369 | $3.5 \times 10^8$ | $8.1 \times 10^7$ | 20,200 |

UNITED STATES PATENT AND TRADEMARK OFFICE
CERTIFICATE OF CORRECTION

PATENT NO. : 5,460,811

DATED : October 24, 1995

INVENTOR(S) : David V. Goeddel and Roberto Crea

In column 14, line 21, please delete t,0220 and insert

Table 2. Interferon activities measured on different cell types

| Cells | Interferon Activity (units/ml) | | |
|---|---|---|---|
| | LeIF | FIF | E. coli K-12 strain 294/pFIFtrp69 extract |
| Human amnion | 20,000 | 10,000 | 1280 |
| Bovine kidney | 13,000 | 400 | 40 |

LeIF and FIF were NIH standard solutions having 20,000 units/ml and 10,000 units/ml respectively. Assays were performed as described in Materials and Methods.

UNITED STATES PATENT AND TRADEMARK OFFICE
CERTIFICATE OF CORRECTION

PATENT NO. : 5,460,811

DATED : October 24, 1995

INVENTOR(S) : David V. Goeddel and Roberto Crea

In column 14, line 21, please delete t,0221 and insert

Table 3. Comparison of activities of extracts from E. coli K-12 strain 294/pFIFtrp69 with standard human leukocyte and fibroblast interferons

|  | Interferon Activity (units/ml) | | |
|---|---|---|---|
|  | LeIF | FIF | E. coli K-12 strain 294/pFIFtrp69 |
| untreated | 1000 | 1000 | 1000 |
| pH2 | 1000 | 1000 | 1000 |
| rabbit antihuman LeIF antibodies | <16 | 1000 | 1000 |

Experimental procedures described in Materials and methods. Assayed by CPE inhibition using WISH cells/Sindbis virus.

Signed and Sealed this

Ninth Day of April, 1996

Attest:

Attesting Officer

BRUCE LEHMAN
Commissioner of Patents and Trademarks